(12) United States Patent
Rajan

(10) Patent No.: US 11,459,552 B2
(45) Date of Patent: Oct. 4, 2022

(54) VARIANT CAS12 PROTEINS WITH IMPROVED DNA CLEAVAGE SELECTIVITY AND METHODS OF USE

(71) Applicant: The Board of Regents of the University of Oklahoma, Norman, OK (US)

(72) Inventor: Rakhi Rajan, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/946,689

(22) Filed: Jul. 1, 2020

(65) Prior Publication Data

US 2020/0332275 A1  Oct. 22, 2020

Related U.S. Application Data

(63) Continuation-in-part of application No. 16/570,555, filed on Sep. 13, 2019, now Pat. No. 11,124,783.

(60) Provisional application No. 62/730,890, filed on Sep. 13, 2018, provisional application No. 62/870,472, filed on Jul. 3, 2019.

(51) Int. Cl.
| | |
|---|---|
| *C12N 9/22* | (2006.01) |
| *C12N 15/113* | (2010.01) |
| *C12N 15/74* | (2006.01) |

(52) U.S. Cl.
CPC .............. *C12N 9/22* (2013.01); *C12N 15/113* (2013.01); *C12N 15/74* (2013.01); *C12N 2310/20* (2017.05); *C12N 2800/80* (2013.01)

(58) Field of Classification Search
CPC .... C12N 9/22; C12N 15/113; C12N 2310/20; C12N 2800/80
See application file for complete search history.

(56) References Cited

U.S. PATENT DOCUMENTS 9,790,490 B2 * 10/2017 Zhang .................... C12N 15/10

OTHER PUBLICATIONS

Whisstock et al. Quaterly Reviews of Biophysics, 2003, "Prediction of protein function from protein sequence and structure", 36(3):307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Zetsche et al. Cpf1 is a Single RNA-Guided Endonuclease of a class 2 CRISPR-Cas system. Cell (2015), 163: 1-13.*
Calnan, B.J., et al.; "Analysis of arginine-rich peptides from the HIV Tat protein reveals unusual features of RNA-protein recognition"; Genes & Development 5 (1991) 201-210.
Ihaka, R., et al.; "R: A Language for Data Analysis and Graphics"; Journal of Computational and Graphical Statistics 5:3 (1996) 299-314.
Weiss, M.A., et al.; "RNA Recognition by Arginine-Rich Peptide Motifs"; Bioploymers (Nucleic Acid Sciences) 48 (1998) 167-180.
DeLano, W.L.; "PyMOL: An Open-Source Molecular Graphics Tool"; DeLano Scientific (2002) 9 pages.
Barrangou, R., et al.; "CRISPR Provides Acquired Resistance Against Viruses in Prokaryotes"; Science 315:5819 (2007) 1709-1712.
Brouns, J.J., et al.; "Small CRISPR RNAs Guide Antiviral Defense in Prokaryotes"; Science 321:5891 (2008) 960-964.
Deveau, H., et al.; "Phage Response to CRISPR-Encoded Resistance in *Streptococcus thermophilus*"; Journal of Bacteriology 190:4 (2008) 1390-1400.
Edelheit, O., et al.; "Simple and efficient site-directed mutagenesis using two single-primer reactions in parallel to generate mutants for protein structure-function studies"; BMC Biotechnology 9:61 (2009) 8 pages.
Gibson, D.G., et al.; "Enzymatic assembly of DNA molecules up to several hundred kilobas1"; Nature Methods 6:5 (2009) 343-347.
Hale, C.R., et al.; "RNA-Guided RNA Cleavage by a CRISPR RNA-Cas Protein Complex"; Cell 139 (2009) 945-956.
Marraffini, L.A., et al.; "Invasive DNA, Chopped and in the CRISPR"; Structure 17 (2009) 786-788.
Garneau, J.E., et al.; "The CRISPR/Cas bacterial immune system cleaves bacteriophage and plasmid DNA"; Nature 468 (2010) 6 pages.
Marraffini, L.A., et al.; "CRISPR interference: RNA-directed adaptive immunity in bacteria and archaea"; Nature Reviews; Genetics 11 (2010) 11 pages.
Marraffini, L.A., et al.; "Self versus non-self discrimination during CRISPR RNA-directed immunity"; Nature 463 (2010) 5 pages.
Gasiumas, G., et al.; "Cas9-crRNA ribonucleoprotein complex mediates specific DNA cleavage for adaptive immunity in bacteria"; PNAS (2012) 8 pages.
Jinek, M., et al.; "A Programmable Dual-RNA-Guided DNA Endonuclease in Adaptive Bacterial Immunity"; Science 337:6096 (2012) 816-821.
Schneider, C.A., et al.; "NIH Image to ImageJ: 25 years of image analysis"; Nature Methods 9:7 (2012) 671-675.
Bachman, J.; "Site-Directed Mutagenesis"; Methods in Enzymology 529 (2013) 241-248.
Casu, F., et al.; "The Arginine-Rich RNA-Binding Motif of HIV-1 Rev Is Intrinsically Disordered and Folds upon RRE Binding"; Biophycial Journal 105 (2013) 1004-1017.
Hou, Z., et al.; "Efficient genome engineering in human pluripotent stem cells using Cas9 from Neisseria memingtiis" National Academy of Sciences 110-39 (2013) 15644-15649.
Mali, P., et al.; "CAS9 transcriptional activators for target specificity screening and paired nickases for cooperative genome engineering"; Nat Biotechnol. 31:9 (2013) 833-838.
Pennisi, E.; "The CRISPR Craze"; Science 341:6148 (2013) 833-836.

(Continued)

*Primary Examiner* — Iqbal H Chowdhury
(74) *Attorney, Agent, or Firm* — Hall Estill Law Firm

(57) ABSTRACT

Bridge helix-modified variant Cas12a and Cas12b proteins having improved DNA cleavage selectivity in comparison to wild type versions of the Cas12a and Cas12b proteins, nucleic acids encoding the variant proteins, host cells containing the nucleic acids, and methods of their use.

10 Claims, 4 Drawing Sheets

Specification includes a Sequence Listing.

(56) References Cited

OTHER PUBLICATIONS

Sampson, T.R., et al.; "Corrigendum: A CRISPR/Cas system mediates bacterial innate immune evasion and virulence"; Nature 501 (2013) 262.

Scholz, J., et al.; "A new method to customize protein expression vectors for fast, efficient and background free parallel cloning"; BMC Biotechnology 13:12 (2013) 12 pages.

Anders, C., et al.; "Structural basis of PAM-dependent target DNA recognition by the Cas9 endonuclease"; Nature 513 (2014) 17 pages.

Brinkman, E.K., et al.; "Easy quantitative assessment of genome editing by sequence trace decomposition"; Nucleic Acids Research 42:22 (2014) 8 pages.

Doudna, J.A., et al.; "Methods in Enzymology. The use of CRISPR/Cas9, ZFNs, and TALENs in generating site-specific genome alternations. Preface. Methods Enzymol"; (2014) xix-xx.

Jinek, M., et al.; "Structures of Cas9 Endonucleases Reveal RNA-Mediated Conformational Activation"; Science 343:6176 (2014) 1215.

Kearns, N.A., et al.; "Cas9 effector-mediated regulation of transcription and differentiation in human pluripotent stem cells"; Development 141 (2014) 219-223.

Nishimasu, H., et al.; "Crystal Structure of Cas9 in Complex with Guide RNA and Target DNA"; Cell 156 (2014) 935-949.

Sternberg, S.H., et al.; "DNA interrogation by the CRISPR RNA-guided endonuclease Cas9"; Nature 507 (2014) 18 pages.

Szczelkun, M.D., et al.; "Direct observation of R-loop formation by single RNA-guided Cas9 and Cascade effector complexes"; National Academy of Sciences 111:27 (2014) 9798-9803.

Tsai, S.Q., et al.; "Dimeric CRISPR RNA-guided FokI nucleases for highly specific genome editing"; Nature Biotechnology 32:6 (2014) 569-576.

Zhou, Y., et al.; "High-throughput screening of a CRISPR/Cas9 library for functional genomics in human cells"; Nature 509 (2014) 487-491.

Bolukbasi, M.F., et al.; "DNA-biding-domain fusions enhance the targeting range and precision of Cas9"; Nature Methods 12:12 (2015) 16 pages.

Xiao-Jie, L., et al.; "CRISPR-Cas9: a new and promising player in gene therapy"; J Med Genet 52 (2015) 289-296.

Doudna, J.A.; Genomic Engineering and the Future of Medicine; JAMA 313:8 (2015) 791-792.

Jiang, F., et al.; "A Cas9-guide RNA complex preorganized for target DNA recognition"; Science 348:6242 (2015) 1477-1481.

Nishimasu, H., et al.; "Crystal Structure of *Staphylococcus aureus* Cas 9"; Cell 162 (2015) 1113-1126.

Sternberg, S.H., et al.; "Conformational control of DNA target cleavage by CRISPR-Cas9"; Nature 527 (2015) 15 pages.

Tsai, S.Q., et al.; "GUIDE-Seq enables genome-wide profiling of off-target cleavage by CRISPR-Cas nucleases"; Nat Biotechnol. 33:2 (2015) 187-197.

Abudayyeh, O.O., et al.; "C2c2 is a single-component programmable RNA-guided RNA-targeting CRISPR effector"; Science 353:6299 (2016) 557; 11 pages.

Hirano, H., et al.; "Structure and Engineering of Francisella novicida Cas9"; Cell 164 (2016) 950-961.

Jiang, F., et al.; "Structures of a CRISPR-Cas9 R-loop complex primed for DNA cleavage"; Science 351:6275 (2016) 9 pages.

Kleinstiver, B.P., et al.; "High-fidelity CRISPR-Cas9 nucleases with no detectable genome-wide off-target effects"; Nature 529 (2016) 36 pages.

Mohanraju, P., et al.; "Diverse evolutionary roots and mechanistic variations of the CRISPR-Cas systems"; Science 353:6299 (2016) 14 pages.

Singh, D., et al.; "Real-time observation of DNA recognition and rejection by the RNA-guided endonuclease Cas9"; Nature Communications (2016) 9 pages.

Slaymaker, I.M., et al.; "Rationally engineered Cas9 nucleases with improved specificity"; Science 351:6268 (2016) 6 pages.

Yang, H.Y., et al.; "PAM-Dependent Target DNA Recognition and Cleavage by C2c1 CRISPR-Cas Endonuclease" Cell 167 (2016) 1814-1828.

Chen, J.S., et al.; "Enhanced proofreading governs CRISPR-Cas9 targeting accuracy"; Nature 550:7676 (2017) 25 pages.

Fogarty, N.M.E., et al.; "Genome editing reveals a role for OCT4 in human embryogenesis"; Nature (2017) 25 pages.

Gaudelli, N.M., et al.; "Programmable base editing of A-T to G-C in genomic DNA without DNA cleavage"; Nature 551:7681 (2017) 37 pages.

Hess, G.T., et al.; "Methods and Applications of CRISPR-Mediated Base Editing in Eukaryotic Genomes"; Molecular Cell 68 (2017) 26-43.

Huai, C., et al.; "Structural insights into DNA cleavage activation of CRISPR-Cas9 system"; Nature Communications 8:1375 (2017) 10 pages.

Koonin, E.V., et al.; "Diversity, classification and evolution of CRISPR-Cas systems"; Current Opinion in Microbiology 37 (2017) 67-78.

Ma, H., et al.; "Correction of a pathogenic gene mutation in human embryos"; Nature 548 (2017) 24 pages.

Shmakov, S., et al.; "Diversity and evolution of class 2 CRISPR-Cas systems"; Nature Reviews; Microbiology 15 (2017) 169-182.

Swarts, D.C., et al.; "Structural Basis for Guide RNA Processing and Seed-Dependent DNA Targeting by CRISPR-Cas 12a"; Molecular Cell 66 (2017) 221-233.

Vriend, L.E.M., et al.; "Nick-initiated homologous recombination: Protecting the genome, one strand at a time"; DNA Repair 50 (2017) 1-13.

Wang, Q., et al.; "Genome modification of CXCR4 by *Staphylococcus aureus* Cas9 renders cells resistance to HIV-1 infection"; Retrovirology 14:51 (2017) 12 pages.

Yamada, M., et al.; "Crystal Structure of the Minimal Cas9 from Campylobacter jejuni Reveals the Molecular Diversity in the CRISPR-Cas9 systems"; Molecular Cell 65 (2017) 1109-1121.

Zuo, Z., et al.; "Structure and Dynamics of Xas9 HNH Domain Catalytic State"; Scientic Reports 7:17271 (2017) 14 pages.

Amrani, N., et al.; "NmeCas9 is an intrinsically high-fidelity genome-editing platform"; Genome Bioloty 19:214 (2018) 25 pages.

Gao, X.D., et al.; "C-BERST: defining subnuclear proteomic landscapes at genomic elements with dCas9-APEX2" Nature Methods 15 (2018) 433-436.

Yang, M., et al.; "The Conformational Dynamics of Cas9 Governing DNA Cleavage Are Revealed by Single-Molecule FRET"; Cell Reports 22 (2018) 372-382.

Zeng, Y., et al.; "The initiation, propagation and dynamics of CRISPR-SpyCas9 R-loop complex"; Nucleic Acids Research 46:1 (2018) 350-361.

* cited by examiner

FnCas12a

*Francisella tularensis subsp. novicida* (strain U112)

MSIYQEFVNKYSLSKTLRFELIPQGKTLENIKARGLILDDEKRAKDYKKAKQIIDKYHQF
FIEEILSSVCISEDLLQNYSDVYFKLKKSDDDNLQKDFKSAKDTIKKQISEYIKDSEKFK
NLFNQNLIDAKKGQESDLILWLKQSKDNGIELFKANSDITDIDEALEIIKSFKGWTTYFK
GFHENRKNVYSSNDIPTSIIYRIVDDNLPKFLENKAKYESLKDKAPEAINYEQIKKDLAE
ELTFDIDYKTSEVNQRVFSLDEVFEIANFNNYLNQSGITKFNTIIGGKFVNGENTKRKGI
NEYINLYSQQINDKTLKKYKMSVLFKQILSDTESKSFVIDKLEDDSDVVTTMQSFYEQIA
AFKTVEEKSIKETLSLLFDDLKAQKLDLSKIYFKNDKSLTDLSQQVFDDYSVIGTAVLEY
ITQQIAPKNLDNPSKKEQELIAKKTEKAKYLSLETIKLALEEFNKHRDIDKQCRFEEILA
NFAAIPMIFDEIAQNKDNLAQISIKYQNQGKKDLLQASAEDDVKAIKDLLDQTNNLLHKL
KIFHISQSEDKANILDKDEHFYLVFEECYFELANIVPLYNKIRNYITQKPYSDEKFKLNF
ENSTLANGWDKNKEPDNTAILFIKDDKYYLGVMNKKNNKIFDDKAIKENKGEGYKKIVYK
LLPGANKMLPKVFFSAKSIKFYNPSEDILRIRNHSTHTKNGSPQKGYEKFEFNIEDCRKF
IDFYKQSISKHPEWKDFGFRFSDTQRYNSIDEFYREVENQGYKLTFENISESYIDSVVNQ
GKLYLFQIYNKDFSAYSKGRPNLHTLYWKALFDERNLQDVVYKLNGEAELFYRKQSIPKK
ITHPAKEAIANKNKDNPKKESVFEYDLIKDKRFTEDKFFFHCPITINFKSSGANKFNDEI
NLLLKEKANDVHILSIDRGERHLAYYTLVDGKGNIIKQDTFNIIGNDRMKTN**YHDKLAAI
EKDRDSARKDW**KKINNIKEMKEGYLSQVVHEIAKLVIEYNAIVVFEDLNFGFKRGRFKVE
KQVYQKLEKMLIEKLNYLVFKDNEFDKTGGVLRAYQLTAPFETFKKMGKQTGIIYYVPAG
FTSKICPVTGFVNQLYPKYESVSKSQEFFSKFDKICYNLDKGYFEFSFDYKNFGDKAAKG
KWTIASFGSRLINFRNSDKNHNWDTREVYPTKELEKLLKDYSIEYGHGECIKAAICGESD
KKFFAKLTSVLNTILQMRNSKTGTELDYLISPVADVNGNFFDSRQAPKNMPQDADANGAY
HIGLKGLMLLGRIKNNQEGKKLNLVIKNEEYFEFVQNRNN

FIG. 1

LbCas12a

*Lachnospiraceae bacterium* ND2006

AASKLEKFTNCYSLSKTLRFKAIPVGKTQENIDNKRLLVEDEKRAEDYKGVKKLLDRYYL
SFINDVLHSIKLKNLNNYISLFRKKTRTEKENKELENLEINLRKEIAKAFKGAAGYKSLF
KKDIIETILPEAADDKDEIALVNSFNGFTTAFTGFFDNRENMFSEEAKSTSIAFRCINEN
LTRYISNMDIFEKVDAIFDKHEVQEIKEKILNSDYDVEDFFEGEFFNFVLTQEGIDVYNA
IIGGFVTESGEKIKGLNEYINLYNAKTKQALPKFKPLYKQVLSDRESLSFYGEGYTSDEE
VLEVFRNTLNKNSEIFSSIKKLEKLFKNFDEYSSAGIFVKNGPAISTISKDIFGEWNLIR
DKWNAEYDDIHLKKKAVVTEKYEDDRRKSFKKIGSFSLEQLQEYADADLSVVEKLKEIII
QKVDEIYKVYGSSEKLFDADFVLEKSLKKNDAVVAIMKDLLDSVKSFENYIKAFFGEGKE
TNRDESFYGDFVLAYDILLKVDHIYDAIRNYVTQKPYSKDKFKLYFQNPQFMGGWDKDKE
TDYRATILRYGSKYYLAIMDKKYAKCLQKIDKDDVNGNYEKINYKLLPGPNKMLPKVFFS
KKWMAYYNPSEDIQKIYKNGTFKKGDMFNLNDCHKLIDFFKDSISRYPKWSNAYDFNFSE
TEKYKDIAGFYREVEEQGYKVSFESASKKEVDKLVEEGKLYMFQIYNKDFSDKSHGTPNL
HTMYFKLLFDENNHGQIRLSGGAELFMRRASLKKEELVVHPANSPIANKNPDNPKKTTTL
SYDVYKDKRFSEDQYELHIPIAINKCPKNIFKINTEVRVLLKHDDNPYVIGIDRGERNLL
YIVVVDGKGNIVEQYSLNEIINNFNGIRIKTDYHSLLDKKEKERFEARQNWTSIENIKEL
KAGYISQVVHKICELVEKYDAVIALEDLNSGFKNSRVKVEKQVYQKFEKMLIDKLNYMVD
KKSNPCATGGALKGYQITNKFESFKSMSTQNGFIFYIPAWLTSKIDPSTGFVNLLKTKYT
SIADSKKFISSFDRIMYVPEEDLFEFALDYKNFSRTDADYIKKWKLYSYGNRIRIFAAAK
KNNVFAWEEVCLTSAYKELFNKYGINYQQGDIRALLCEQSDKAFYSSFMALMSLMLQMRN
SITGRTDVDFLISPVKNSDGIFYDSRNYEAQENAILPKNADANGAYNIARKVLWAIGQFK
KAEDEKLDKVKIAISNKEWLEYAQTSVK

FIG. 2

AsCas12a

*Acidaminococcus sp.* (strain BV3L6)

```
MTQFEGFTNLYQVSKTLRFELIPQGKTLKHIQEQGFIEEDKARNDHYKELKPIIDRIYKT
YADQCLQLVQLDWENLSAAIDSYRKEKTEETRNALIEEQATYRNAIHDYFIGRTDNLTDA
INKRHAEIYKGLFKAELFNGKVLKQLGTVTTTEHENALLRSFDKFTTYFSGFYENRKNVF
SAEDISTAIPHRIVQDNFPKFKENCHIFTRLITAVPSLREHFENVKKAIGIFVSTSIEEV
FSFPFYNQLLTQTQIDLYNQLLGGISREAGTEKIKGLNEVLNLAIQKNDETAHIIASLPH
RFIPLFKQILSDRNTLSFILEEFKSDEEVIQSFCKYKTLLRNENVLETAEALFNELNSID
LTHIFISHKKLETISSALCDHWDTLRNALYERRISELTGKITKSAKEKVQRSLKHEDINL
QEIISAAGKELSEAFKQKTSEILSHAHAALDQPLPTTLKKQEEKEILKSQLDSLLGLYHL
LDWFAVDESNEVDPEFSARLTGIKLEMEPSLSFYNKARNYATKKPYSVEKFKLNFQMPTL
ASGWDVNKEKNNGAILFVKNGLYYLGIMPKQKGRYKALSFEPTEKTSEGFDKMYYDYFPD
AAKMIPKCSTQLKAVTAHFQTHTTPILLSNNFIEPLEITKEIYDLNNPEKEPKKFQTAYA
KKTGDQKGYREALCKWIDFTRDFLSKYTKTTSIDLSSLRPSSQYKDLGEYYAELNPLLYH
ISFQRIAEKEIMDAVETGKLYLFQIYNKDFAKGHHGKPNLHTLYWTGLFSPENLAKTSIK
LNGQAELFYRPKSRMKRMAHRLGEKMLNKKLKDQKTPIPDTLYQELYDYVNHRLSHDLSD
EARALLPNVITKEVSHEIIKDRRFTSDKFFFHVPITLNYQAANSPSKFNQRVNAYLKEHP
ETPIIGIDRGERNLIYITVIDSTGKILEQRSLNTIQQFDYQKKLDNREKERVAARQAWSV
VGTIKDLKQGYLSQVIHEIVDLMIHYQAVVVLENLNFGFKSKRTGIAEKAVYQQFEKMLI
DKLNCLVLKDYPAEKVGGVLNPYQLTDQFTSFAKMGTQSGFLFYVPAPYTSKIDPLTGFV
DPFVWKTIKNHESRKHFLEGFDFLHYDVKTGDFILHFKMNRNLSFQRGLPGFMPAWDIVF
EKNETQFDAKGTPFIAGKRIVPVIENHRFTGRYRDLYPANELIALLEEKGIVFRDGSNIL
PKLLENDDSHAIDTMVALIRSVLQMRNSNAATGEDYINSPVRDLNGVCFDSRFQNPEWPM
DADANGAYHIALKGQLLLNHLKESKDLKLQNGISNQDWLAYIQELRN
```

FIG. 3

AaCas12b

*Alicyclobacillus acidoterrestris* strain 49025

MAVKSIKVKLRLDDMPEIRAGLWKLHKEVNAGVRYYTEWLSLLRQENLYRRSPNGDGEQE
CDKTAEECKAELLERLRARQVENGHRGPAGSDDELLQLARQLYELLVPQAIGAKGDAQQI
ARKFLSPLADKDAVGGLGIAKAGNKPRWVRMREAGEPGWEEEKEKAETRKSADRTADVLR
ALADFGLKPLMRVYTDSEMSSVEWKPLRKGQAVRTWDRDMFQQAIERMMSWESWNQRVGQ
EYAKLVEQKNRFEQKNFVGQEHLVHLVNQLQQDMKEASPGLESKEQTAHYVTGRALRGSD
KVFEKWGKLAPDAPFDLYDAEIKNVQRRNTRRFGSHDLFAKLAEPEYQALWREDASFLTR
YAVYNSILRKLNHAKMFATFTLPDATAHPIWTRFDKLGGNLHQYTFLFNEFGERRHAIRF
HKLLKVENGVAREVDDVTVPISMSEQLDNLLPRDPNEPIALYFRDYGAEQHFTGEFGGAK
IQCRRDQLAHMHRRRGARDVYLNVSVRVQSQSEARGERRPPYAAVFRLVGDNHRAFVHFD
KLSDYLAEHPDDGKLGSEGLLSGLRVMSVDLGLRTSASISVFRVARKDELKPNSKGRVPF
FFPIKGNDNLVAVHERSQLLKLPGETESKDLRAIREERQRTLRQLRTQLAYLRLLVRCGS
EDVGRRERSWAKLIEQPVDAANHMTPDWREAFENELQKLKSLHGICSDKEWMDAVYESVR
RVWRHMGKQVRDWRKDVRSGERPKIRGYAKDVVGGNSIEQIEYLERQYKFLKSWSFFGKV
SGQVIRAEKGSRFAITLREHIDHAKEDRLKKLADRIIMEALGYVYALDERGKGKWVAKYP
PCQLILLEELSEYQFNNDRPPSENNQLMQWSHRGVFQELINQAQVHDLLVGTMYAAFSSR
FDARTGAPGIRCRRVPARCTQEHNPEPFPWWLNKFVVEHTLDACPLRADDLIPTGEGEIF
VSPFSAEEGDFHQIHADLNAAQNLQQRLWSDFDISQIRLRCDWGEVDGELVLIPRLTGKR
TADSYSNKVFYTNTGVTYYERERGKKRRKVFAQEKLSEEEAELLVEADEAREKSVVLMRD
PSGIINRGNWTRQKEFWSMVNQRIEGYLVKQIRSRVPLQDSACENTGDI

FIG. 4

SEQUENCE LISTING

<160> NUMBER OF SEQ ID NOS: 4

<210> SEQ ID NO 1
<211> LENGTH: 1300
<212> TYPE: PRT
<213> ORGANISM: Francisella tularensis subsp. novicida (strain U112)

<400> SEQUENCE: 1

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
            85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
            115                 120                 125

Asp Ala Lys Lys Gly Gln Glu Ser Asp Leu Ile Leu Trp Leu Lys Gln
        130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
            165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
            195                 200                 205

Pro Lys Phe Leu Glu Asn Lys Ala Lys Tyr Glu Ser Leu Lys Asp Lys
        210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
            245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285
```

-continued

```
Phe Val Asn Gly Glu Asn Thr Lys Arg Lys Gly Ile Asn Glu Tyr Ile
    290                 295                 300
Asn Leu Tyr Ser Gln Gln Ile Asn Asp Lys Thr Leu Lys Lys Tyr Lys
305                 310                 315                 320
Met Ser Val Leu Phe Lys Gln Ile Leu Ser Asp Thr Glu Ser Lys Ser
                325                 330                 335
Phe Val Ile Asp Lys Leu Glu Asp Asp Ser Asp Val Val Thr Thr Met
            340                 345                 350
Gln Ser Phe Tyr Glu Gln Ile Ala Ala Phe Lys Thr Val Glu Glu Lys
        355                 360                 365
Ser Ile Lys Glu Thr Leu Ser Leu Leu Phe Asp Asp Leu Lys Ala Gln
    370                 375                 380
Lys Leu Asp Leu Ser Lys Ile Tyr Phe Lys Asn Asp Lys Ser Leu Thr
385                 390                 395                 400
Asp Leu Ser Gln Gln Val Phe Asp Asp Tyr Ser Val Ile Gly Thr Ala
                405                 410                 415
Val Leu Glu Tyr Ile Thr Gln Gln Ile Ala Pro Lys Asn Leu Asp Asn
            420                 425                 430
Pro Ser Lys Lys Glu Gln Glu Leu Ile Ala Lys Lys Thr Glu Lys Ala
        435                 440                 445
Lys Tyr Leu Ser Leu Glu Thr Ile Lys Leu Ala Leu Glu Glu Phe Asn
    450                 455                 460
Lys His Arg Asp Ile Asp Lys Gln Cys Arg Phe Glu Glu Ile Leu Ala
465                 470                 475                 480
Asn Phe Ala Ala Ile Pro Met Ile Phe Asp Glu Ile Ala Gln Asn Lys
                485                 490                 495
Asp Asn Leu Ala Gln Ile Ser Ile Lys Tyr Gln Asn Gln Gly Lys Lys
            500                 505                 510
Asp Leu Leu Gln Ala Ser Ala Glu Asp Val Lys Ala Ile Lys Asp
        515                 520                 525
Leu Leu Asp Gln Thr Asn Asn Leu Leu His Lys Leu Lys Ile Phe His
    530                 535                 540
Ile Ser Gln Ser Glu Asp Lys Ala Asn Ile Leu Asp Lys Asp Glu His
545                 550                 555                 560
Phe Tyr Leu Val Phe Glu Glu Cys Tyr Phe Glu Leu Ala Asn Ile Val
                565                 570                 575
Pro Leu Tyr Asn Lys Ile Arg Asn Tyr Ile Thr Gln Lys Pro Tyr Ser
            580                 585                 590
Asp Glu Lys Phe Lys Leu Asn Phe Glu Asn Ser Thr Leu Ala Asn Gly
        595                 600                 605
Trp Asp Lys Asn Lys Glu Pro Asp Asn Thr Ala Ile Leu Phe Ile Lys
    610                 615                 620
Asp Asp Lys Tyr Tyr Leu Gly Val Met Asn Lys Lys Asn Asn Lys Ile
625                 630                 635                 640
Phe Asp Asp Lys Ala Ile Lys Glu Asn Lys Gly Glu Gly Tyr Lys Lys
                645                 650                 655
Ile Val Tyr Lys Leu Leu Pro Gly Ala Asn Lys Met Leu Pro Lys Val
            660                 665                 670
Phe Phe Ser Ala Lys Ser Ile Lys Phe Tyr Asn Pro Ser Glu Asp Ile
        675                 680                 685
Leu Arg Ile Arg Asn His Ser Thr His Thr Lys Asn Gly Ser Pro Gln
    690                 695                 700
```

```
Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
            725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
            755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
                820                 825                 830

Arg Lys Gln Ser Ile Pro Lys Lys Ile Thr His Pro Ala Lys Glu Ala
                835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
                915                 920                 925

Val Asp Gly Lys Gly Asn Ile Ile Lys Gln Asp Thr Phe Asn Ile Ile
                930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn Ala Ile Val Val Phe Glu Asp Leu
                995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
```

```
                1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300

<210> SEQ ID NO 2
<211> LENGTH: 1228
<212> TYPE: PRT
<213> ORGANISM: Lachnospiraceae bacterium ND2006

<400> SEQUENCE: 2

Ala Ala Ser Lys Leu Glu Lys Phe Thr Asn Cys Tyr Ser Leu Ser Lys
1               5                   10                  15

Thr Leu Arg Phe Lys Ala Ile Pro Val Gly Lys Thr Gln Glu Asn Ile
            20                  25                  30

Asp Asn Lys Arg Leu Leu Val Glu Asp Glu Lys Arg Ala Glu Asp Tyr
        35                  40                  45

Lys Gly Val Lys Lys Leu Leu Asp Arg Tyr Tyr Leu Ser Phe Ile Asn
    50                  55                  60

Asp Val Leu His Ser Ile Lys Leu Lys Asn Leu Asn Asn Tyr Ile Ser
65                  70                  75                  80

Leu Phe Arg Lys Lys Thr Arg Thr Glu Lys Glu Asn Lys Glu Leu Glu
                85                  90                  95

Asn Leu Glu Ile Asn Leu Arg Lys Glu Ile Ala Lys Ala Phe Lys Gly
            100                 105                 110

Ala Ala Gly Tyr Lys Ser Leu Phe Lys Lys Asp Ile Ile Glu Thr Ile
        115                 120                 125

Leu Pro Glu Ala Ala Asp Asp Lys Asp Glu Ile Ala Leu Val Asn Ser
    130                 135                 140

Phe Asn Gly Phe Thr Thr Ala Phe Thr Gly Phe Phe Asp Asn Arg Glu
145                 150                 155                 160

Asn Met Phe Ser Glu Glu Ala Lys Ser Thr Ser Ile Ala Phe Arg Cys
                165                 170                 175
```

-continued

```
Ile Asn Glu Asn Leu Thr Arg Tyr Ile Ser Asn Met Asp Ile Phe Glu
            180                 185                 190

Lys Val Asp Ala Ile Phe Asp Lys His Glu Val Gln Glu Ile Lys Glu
        195                 200                 205

Lys Ile Leu Asn Ser Asp Tyr Asp Val Glu Asp Phe Phe Glu Gly Glu
    210                 215                 220

Phe Phe Asn Phe Val Leu Thr Gln Glu Gly Ile Asp Val Tyr Asn Ala
225                 230                 235                 240

Ile Ile Gly Gly Phe Val Thr Glu Ser Gly Lys Ile Lys Gly Leu
                245                 250                 255

Asn Glu Tyr Ile Asn Leu Tyr Asn Ala Lys Thr Lys Gln Ala Leu Pro
            260                 265                 270

Lys Phe Lys Pro Leu Tyr Lys Gln Val Leu Ser Asp Arg Glu Ser Leu
        275                 280                 285

Ser Phe Tyr Gly Glu Gly Tyr Thr Ser Asp Glu Glu Val Leu Glu Val
    290                 295                 300

Phe Arg Asn Thr Leu Asn Lys Asn Ser Glu Ile Phe Ser Ser Ile Lys
305                 310                 315                 320

Lys Leu Glu Lys Leu Phe Lys Asn Phe Asp Glu Tyr Ser Ser Ala Gly
                325                 330                 335

Ile Phe Val Lys Asn Gly Pro Ala Ile Ser Thr Ile Ser Lys Asp Ile
            340                 345                 350

Phe Gly Glu Trp Asn Leu Ile Arg Asp Lys Trp Asn Ala Glu Tyr Asp
        355                 360                 365

Asp Ile His Leu Lys Lys Ala Val Val Thr Glu Lys Tyr Glu Asp
    370                 375                 380

Asp Arg Arg Lys Ser Phe Lys Lys Ile Gly Ser Phe Ser Leu Glu Gln
385                 390                 395                 400

Leu Gln Glu Tyr Ala Asp Ala Asp Leu Ser Val Val Glu Lys Leu Lys
                405                 410                 415

Glu Ile Ile Ile Gln Lys Val Asp Glu Ile Tyr Lys Val Tyr Gly Ser
            420                 425                 430

Ser Glu Lys Leu Phe Asp Ala Asp Phe Val Leu Glu Lys Ser Leu Lys
        435                 440                 445

Lys Asn Asp Ala Val Val Ala Ile Met Lys Asp Leu Leu Asp Ser Val
    450                 455                 460

Lys Ser Phe Glu Asn Tyr Ile Lys Ala Phe Phe Gly Glu Gly Lys Glu
465                 470                 475                 480

Thr Asn Arg Asp Glu Ser Phe Tyr Gly Asp Phe Val Leu Ala Tyr Asp
                485                 490                 495

Ile Leu Leu Lys Val Asp His Ile Tyr Asp Ala Ile Arg Asn Tyr Val
            500                 505                 510

Thr Gln Lys Pro Tyr Ser Lys Asp Lys Phe Lys Leu Tyr Phe Gln Asn
        515                 520                 525

Pro Gln Phe Met Gly Gly Trp Asp Lys Asp Lys Glu Thr Asp Tyr Arg
    530                 535                 540

Ala Thr Ile Leu Arg Tyr Gly Ser Lys Tyr Tyr Leu Ala Ile Met Asp
545                 550                 555                 560

Lys Lys Tyr Ala Lys Cys Leu Gln Lys Ile Asp Lys Asp Asp Val Asn
                565                 570                 575

Gly Asn Tyr Glu Lys Ile Asn Tyr Lys Leu Leu Pro Gly Pro Asn Lys
            580                 585                 590

Met Leu Pro Lys Val Phe Phe Ser Lys Lys Trp Met Ala Tyr Tyr Asn
```

```
            595                 600                 605
Pro Ser Glu Asp Ile Gln Lys Ile Tyr Lys Asn Gly Thr Phe Lys Lys
610                 615                 620

Gly Asp Met Phe Asn Leu Asn Asp Cys His Lys Leu Ile Asp Phe Phe
625                 630                 635                 640

Lys Asp Ser Ile Ser Arg Tyr Pro Lys Trp Ser Asn Ala Tyr Asp Phe
                645                 650                 655

Asn Phe Ser Glu Thr Glu Lys Tyr Lys Asp Ile Ala Gly Phe Tyr Arg
                660                 665                 670

Glu Val Glu Glu Gln Gly Tyr Lys Val Ser Phe Glu Ser Ala Ser Lys
                675                 680                 685

Lys Glu Val Asp Lys Leu Val Glu Glu Gly Lys Leu Tyr Met Phe Gln
690                 695                 700

Ile Tyr Asn Lys Asp Phe Ser Asp Lys Ser His Gly Thr Pro Asn Leu
705                 710                 715                 720

His Thr Met Tyr Phe Lys Leu Leu Phe Asp Glu Asn Asn His Gly Gln
                725                 730                 735

Ile Arg Leu Ser Gly Gly Ala Glu Leu Phe Met Arg Arg Ala Ser Leu
                740                 745                 750

Lys Lys Glu Glu Leu Val Val His Pro Ala Asn Ser Pro Ile Ala Asn
                755                 760                 765

Lys Asn Pro Asp Asn Pro Lys Lys Thr Thr Thr Leu Ser Tyr Asp Val
770                 775                 780

Tyr Lys Asp Lys Arg Phe Ser Glu Asp Gln Tyr Glu Leu His Ile Pro
785                 790                 795                 800

Ile Ala Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
                820                 825                 830

Asp Arg Gly Glu Arg Asn Leu Leu Tyr Ile Val Val Val Asp Gly Lys
                835                 840                 845

Gly Asn Ile Val Glu Gln Tyr Ser Leu Asn Glu Ile Ile Asn Asn Phe
850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
                885                 890                 895

Ile Lys Glu Leu Lys Ala Gly Tyr Ile Ser Gln Val Val His Lys Ile
                900                 905                 910

Cys Glu Leu Val Glu Lys Tyr Asp Ala Val Ile Ala Leu Glu Asp Leu
                915                 920                 925

Asn Ser Gly Phe Lys Asn Ser Arg Val Lys Val Glu Lys Gln Val Tyr
930                 935                 940

Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
                965                 970                 975

Ile Thr Asn Lys Phe Glu Ser Phe Lys Ser Met Ser Thr Gln Asn Gly
                980                 985                 990

Phe Ile Phe Tyr Ile Pro Ala Trp Leu Thr Ser Lys Ile Asp Pro Ser
                995                 1000                1005

Thr Gly Phe Val Asn Leu Leu Lys Thr Lys Tyr Thr Ser Ile Ala
            1010                1015                1020
```

```
Asp Ser Lys Lys Phe Ile Ser  Ser Phe Asp Arg Ile  Met Tyr Val
    1025              1030                 1035

Pro Glu Glu Asp Leu Phe Glu  Phe Ala Leu Asp Tyr  Lys Asn Phe
    1040              1045                 1050

Ser Arg Thr Asp Ala Asp Tyr  Ile Lys Lys Trp Lys  Leu Tyr Ser
    1055              1060                 1065

Tyr Gly Asn Arg Ile Arg Ile  Phe Ala Ala Ala Lys  Lys Asn Asn
    1070              1075                 1080

Val Phe Ala Trp Glu Glu Val  Cys Leu Thr Ser Ala  Tyr Lys Glu
    1085              1090                 1095

Leu Phe Asn Lys Tyr Gly Ile  Asn Tyr Gln Gln Gly  Asp Ile Arg
    1100              1105                 1110

Ala Leu Leu Cys Glu Gln Ser  Asp Lys Ala Phe Tyr  Ser Ser Phe
    1115              1120                 1125

Met Ala Leu Met Ser Leu Met  Leu Gln Met Arg Asn  Ser Ile Thr
    1130              1135                 1140

Gly Arg Thr Asp Val Asp Phe  Leu Ile Ser Pro Val  Lys Asn Ser
    1145              1150                 1155

Asp Gly Ile Phe Tyr Asp Ser  Arg Asn Tyr Glu Ala  Gln Glu Asn
    1160              1165                 1170

Ala Ile Leu Pro Lys Asn Ala  Asp Ala Asn Gly Ala  Tyr Asn Ile
    1175              1180                 1185

Ala Arg Lys Val Leu Trp Ala  Ile Gly Gln Phe Lys  Lys Ala Glu
    1190              1195                 1200

Asp Glu Lys Leu Asp Lys Val  Lys Ile Ala Ile Ser  Asn Lys Glu
    1205              1210                 1215

Trp Leu Glu Tyr Ala Gln Thr  Ser Val Lys
    1220              1225

<210> SEQ ID NO 3
<211> LENGTH: 1307
<212> TYPE: PRT
<213> ORGANISM: Acidaminococcus sp. (strain BV3L6)

<400> SEQUENCE: 3

Met Thr Gln Phe Glu Gly Phe  Thr Asn Leu Tyr Gln  Val Ser Lys Thr
1               5                  10                  15

Leu Arg Phe Glu Leu Ile Pro  Gln Gly Lys Thr Leu  Lys His Ile Gln
                20                  25                  30

Glu Gln Gly Phe Ile Glu Glu  Asp Lys Ala Arg Asn  Asp His Tyr Lys
            35                  40                  45

Glu Leu Lys Pro Ile Ile Asp  Arg Ile Tyr Lys Thr  Tyr Ala Asp Gln
        50                  55                  60

Cys Leu Gln Leu Val Gln Leu  Asp Trp Glu Asn Leu  Ser Ala Ala Ile
65                  70                  75                  80

Asp Ser Tyr Arg Lys Lys Thr  Glu Glu Thr Arg Asn  Ala Leu Ile
                85                  90                  95

Glu Glu Gln Ala Thr Tyr Arg  Asn Ala Ile His Asp  Tyr Phe Ile Gly
            100                 105                 110

Arg Thr Asp Asn Leu Thr Asp  Ala Ile Asn Lys Arg  His Ala Glu Ile
        115                 120                 125

Tyr Lys Gly Leu Phe Lys Ala  Glu Leu Phe Asn Gly  Lys Val Leu Lys
    130                 135                 140

Gln Leu Gly Thr Val Thr Thr  Thr Glu His Glu Asn  Ala Leu Leu Arg
```

```
            145                 150                 155                 160
Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
                195                 200                 205

Thr Arg Leu Ile Thr Ala Val Pro Ser Leu Arg Glu His Phe Glu Asn
        210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
        290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
        370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
        450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
                530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575
```

```
Ala Leu Ser Phe Glu Pro Thr Glu Lys Thr Ser Gly Phe Asp Lys
            580                 585                 590

Met Tyr Tyr Asp Tyr Phe Pro Asp Ala Ala Lys Met Ile Pro Lys Cys
            595                 600                 605

Ser Thr Gln Leu Lys Ala Val Thr Ala His Phe Gln Thr His Thr Thr
            610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
            690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
            770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
            930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990
```

Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
        1010                1015                1020

Asn Cys Leu Val Leu Lys Asp Tyr Pro Ala Glu Lys Val Gly Gly
        1025                1030                1035

Val Leu Asn Pro Tyr Gln Leu Thr Asp Gln Phe Thr Ser Phe Ala
        1040                1045                1050

Lys Met Gly Thr Gln Ser Gly Phe Leu Phe Tyr Val Pro Ala Pro
        1055                1060                1065

Tyr Thr Ser Lys Ile Asp Pro Leu Thr Gly Phe Val Asp Pro Phe
        1070                1075                1080

Val Trp Lys Thr Ile Lys Asn His Glu Ser Arg Lys His Phe Leu
        1085                1090                1095

Glu Gly Phe Asp Phe Leu His Tyr Asp Val Lys Thr Gly Asp Phe
        1100                1105                1110

Ile Leu His Phe Lys Met Asn Arg Asn Leu Ser Phe Gln Arg Gly
        1115                1120                1125

Leu Pro Gly Phe Met Pro Ala Trp Asp Ile Val Phe Glu Lys Asn
        1130                1135                1140

Glu Thr Gln Phe Asp Ala Lys Gly Thr Pro Phe Ile Ala Gly Lys
        1145                1150                1155

Arg Ile Val Pro Val Ile Glu Asn His Arg Phe Thr Gly Arg Tyr
        1160                1165                1170

Arg Asp Leu Tyr Pro Ala Asn Glu Leu Ile Ala Leu Leu Glu Glu
        1175                1180                1185

Lys Gly Ile Val Phe Arg Asp Gly Ser Asn Ile Leu Pro Lys Leu
        1190                1195                1200

Leu Glu Asn Asp Asp Ser His Ala Ile Asp Thr Met Val Ala Leu
        1205                1210                1215

Ile Arg Ser Val Leu Gln Met Arg Asn Ser Asn Ala Ala Thr Gly
        1220                1225                1230

Glu Asp Tyr Ile Asn Ser Pro Val Arg Asp Leu Asn Gly Val Cys
        1235                1240                1245

Phe Asp Ser Arg Phe Gln Asn Pro Glu Trp Pro Met Asp Ala Asp
        1250                1255                1260

Ala Asn Gly Ala Tyr His Ile Ala Leu Lys Gly Gln Leu Leu Leu
        1265                1270                1275

Asn His Leu Lys Glu Ser Lys Asp Leu Lys Leu Gln Asn Gly Ile
        1280                1285                1290

Ser Asn Gln Asp Trp Leu Ala Tyr Ile Gln Glu Leu Arg Asn
        1295                1300                1305

<210> SEQ ID NO 4
<211> LENGTH: 1129
<212> TYPE: PRT
<213> ORGANISM: Alicyclobacillus acidoterrestris (strain 49025)

<400> SEQUENCE: 4

Met Ala Val Lys Ser Ile Lys Val Lys Leu Arg Leu Asp Asp Met Pro
1               5                   10                  15

Glu Ile Arg Ala Gly Leu Trp Lys Leu His Lys Glu Val Asn Ala Gly
            20                  25                  30

Val Arg Tyr Tyr Thr Glu Trp Leu Ser Leu Leu Arg Gln Glu Asn Leu
        35                  40                  45

```
Tyr Arg Arg Ser Pro Asn Gly Asp Gly Glu Gln Cys Asp Lys Thr
     50              55              60

Ala Glu Glu Cys Lys Ala Glu Leu Leu Glu Arg Leu Arg Ala Arg Gln
 65              70              75              80

Val Glu Asn Gly His Arg Gly Pro Ala Gly Ser Asp Asp Glu Leu Leu
                 85              90              95

Gln Leu Ala Arg Gln Leu Tyr Glu Leu Leu Val Pro Gln Ala Ile Gly
             100             105             110

Ala Lys Gly Asp Ala Gln Gln Ile Ala Arg Lys Phe Leu Ser Pro Leu
         115             120             125

Ala Asp Lys Asp Ala Val Gly Gly Leu Gly Ile Ala Lys Ala Gly Asn
     130             135             140

Lys Pro Arg Trp Val Arg Met Arg Glu Ala Gly Glu Pro Gly Trp Glu
145             150             155             160

Glu Glu Lys Glu Lys Ala Glu Thr Arg Lys Ser Ala Asp Arg Thr Ala
                 165             170             175

Asp Val Leu Arg Ala Leu Ala Asp Phe Gly Leu Lys Pro Leu Met Arg
             180             185             190

Val Tyr Thr Asp Ser Glu Met Ser Ser Val Glu Trp Lys Pro Leu Arg
         195             200             205

Lys Gly Gln Ala Val Arg Thr Trp Asp Arg Asp Met Phe Gln Gln Ala
     210             215             220

Ile Glu Arg Met Met Ser Trp Glu Ser Trp Asn Gln Arg Val Gly Gln
225             230             235             240

Glu Tyr Ala Lys Leu Val Glu Gln Lys Asn Arg Phe Glu Gln Lys Asn
                 245             250             255

Phe Val Gly Gln Glu His Leu Val His Leu Val Asn Gln Leu Gln Gln
             260             265             270

Asp Met Lys Glu Ala Ser Pro Gly Leu Glu Ser Lys Glu Gln Thr Ala
         275             280             285

His Tyr Val Thr Gly Arg Ala Leu Arg Gly Ser Asp Lys Val Phe Glu
     290             295             300

Lys Trp Gly Lys Leu Ala Pro Asp Ala Pro Phe Asp Leu Tyr Asp Ala
305             310             315             320

Glu Ile Lys Asn Val Gln Arg Arg Asn Thr Arg Arg Phe Gly Ser His
                 325             330             335

Asp Leu Phe Ala Lys Leu Ala Glu Pro Glu Tyr Gln Ala Leu Trp Arg
             340             345             350

Glu Asp Ala Ser Phe Leu Thr Arg Tyr Ala Val Tyr Asn Ser Ile Leu
         355             360             365

Arg Lys Leu Asn His Ala Lys Met Phe Ala Thr Phe Thr Leu Pro Asp
     370             375             380

Ala Thr Ala His Pro Ile Trp Thr Arg Phe Asp Lys Leu Gly Gly Asn
385             390             395             400

Leu His Gln Tyr Thr Phe Leu Phe Asn Glu Phe Gly Glu Arg Arg His
                 405             410             415

Ala Ile Arg Phe His Lys Leu Leu Lys Val Glu Asn Gly Val Ala Arg
             420             425             430

Glu Val Asp Asp Val Thr Val Pro Ile Ser Met Ser Glu Gln Leu Asp
         435             440             445

Asn Leu Leu Pro Arg Asp Pro Asn Glu Pro Ile Ala Leu Tyr Phe Arg
     450             455             460
```

```
Asp Tyr Gly Ala Glu Gln His Phe Thr Gly Glu Phe Gly Gly Ala Lys
465                 470                 475                 480

Ile Gln Cys Arg Arg Asp Gln Leu Ala His Met His Arg Arg Arg Gly
                485                 490                 495

Ala Arg Asp Val Tyr Leu Asn Val Ser Val Arg Val Gln Ser Gln Ser
            500                 505                 510

Glu Ala Arg Gly Glu Arg Arg Pro Tyr Ala Ala Val Phe Arg Leu
        515                 520                 525

Val Gly Asp Asn His Arg Ala Phe Val His Phe Asp Lys Leu Ser Asp
    530                 535                 540

Tyr Leu Ala Glu His Pro Asp Asp Gly Lys Leu Gly Ser Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
            580                 585                 590

Asn Ser Lys Gly Arg Val Pro Phe Phe Pro Ile Lys Gly Asn Asp
    595                 600                 605

Asn Leu Val Ala Val His Glu Arg Ser Gln Leu Leu Lys Leu Pro Gly
    610                 615                 620

Glu Thr Glu Ser Lys Asp Leu Arg Ala Ile Arg Glu Arg Gln Arg
625                 630                 635                 640

Thr Leu Arg Gln Leu Arg Thr Gln Leu Ala Tyr Leu Arg Leu Val
                645                 650                 655

Arg Cys Gly Ser Glu Asp Val Gly Arg Arg Glu Arg Ser Trp Ala Lys
                660                 665                 670

Leu Ile Glu Gln Pro Val Asp Ala Ala Asn His Met Thr Pro Asp Trp
    675                 680                 685

Arg Glu Ala Phe Glu Asn Glu Leu Gln Lys Leu Lys Ser Leu His Gly
    690                 695                 700

Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val
            740                 745                 750

Val Gly Gly Asn Ser Ile Glu Gln Ile Glu Tyr Leu Glu Arg Gln Tyr
    755                 760                 765

Lys Phe Leu Lys Ser Trp Ser Phe Phe Gly Lys Val Ser Gly Gln Val
770                 775                 780

Ile Arg Ala Glu Lys Gly Ser Arg Phe Ala Ile Thr Leu Arg Glu His
785                 790                 795                 800

Ile Asp His Ala Lys Glu Asp Arg Leu Lys Lys Leu Ala Asp Arg Ile
                805                 810                 815

Ile Met Glu Ala Leu Gly Tyr Val Tyr Ala Leu Asp Glu Arg Gly Lys
            820                 825                 830

Gly Lys Trp Val Ala Lys Tyr Pro Pro Cys Gln Leu Ile Leu Leu Glu
            835                 840                 845

Glu Leu Ser Glu Tyr Gln Phe Asn Asn Asp Arg Pro Pro Ser Glu Asn
            850                 855                 860

Asn Gln Leu Met Gln Trp Ser His Arg Gly Val Phe Gln Glu Leu Ile
865                 870                 875                 880

Asn Gln Ala Gln Val His Asp Leu Leu Val Gly Thr Met Tyr Ala Ala
```

-continued

```
                885                 890                 895
Phe Ser Ser Arg Phe Asp Ala Arg Thr Gly Ala Pro Gly Ile Arg Cys
            900                 905                 910

Arg Arg Val Pro Ala Arg Cys Thr Gln Glu His Asn Pro Glu Pro Phe
        915                 920                 925

Pro Trp Trp Leu Asn Lys Phe Val Val Glu His Thr Leu Asp Ala Cys
    930                 935                 940

Pro Leu Arg Ala Asp Asp Leu Ile Pro Thr Gly Glu Gly Glu Ile Phe
945                 950                 955                 960

Val Ser Pro Phe Ser Ala Glu Glu Gly Asp Phe His Gln Ile His Ala
                965                 970                 975

Asp Leu Asn Ala Ala Gln Asn Leu Gln Gln Arg Leu Trp Ser Asp Phe
                980                 985                 990

Asp Ile Ser Gln Ile Arg Leu Arg  Cys Asp Trp Gly Glu  Val Asp Gly
            995                 1000                1005

Glu Leu Val Leu Ile Pro Arg  Leu Thr Gly Lys Arg  Thr Ala Asp
        1010                1015                1020

Ser Tyr Ser Asn Lys Val Phe  Tyr Thr Asn Thr Gly  Val Thr Tyr
        1025                1030                1035

Tyr Glu Arg Glu Arg Gly Lys  Lys Arg Arg Lys Val  Phe Ala Gln
        1040                1045                1050

Glu Lys Leu Ser Glu Glu Glu  Ala Glu Leu Leu Val  Glu Ala Asp
        1055                1060                1065

Glu Ala Arg Glu Lys Ser Val  Val Leu Met Arg Asp  Pro Ser Gly
        1070                1075                1080

Ile Ile Asn Arg Gly Asn Trp  Thr Arg Gln Lys Glu  Phe Trp Ser
        1085                1090                1095

Met Val Asn Gln Arg Ile Glu  Gly Tyr Leu Val Lys  Gln Ile Arg
        1100                1105                1110

Ser Arg Val Pro Leu Gln Asp  Ser Ala Cys Glu Asn  Thr Gly Asp
        1115                1120                1125

Ile
```

VARIANT CAS12 PROTEINS WITH IMPROVED DNA CLEAVAGE SELECTIVITY AND METHODS OF USE

CROSS REFERENCE TO RELATED APPLICATIONS

The present patent application is a continuation-in-part of U.S. Ser. No. 16/570,555, filed Sep. 13, 2019, which claims priority to United States Provisional Patent Application Ser. Nos. 62/730,890, filed on Sep. 13, 2018, and 62/870,472, filed on Jul. 3, 2019, the entireties of which are hereby expressly incorporated herein by reference.

GOVERNMENT SUPPORT

This invention was made with government support under National Science Foundation Grant MCB-1716423 and National Institutes of Health Grant P20GM103640. The government has certain rights in the invention.

BACKGROUND

CRISPR-Cas (clustered regularly interspaced short palindromic repeats-CRISPR associated) systems are RNA-guided nucleic acid targeting machinery in bacteria and archaea that provide adaptive immunity against intruding genomic materials such as phages. These systems have been repurposed into powerful gene editing tools over the past decade. Cas9 and Cas12a are two proteins from the CRISPR systems that are currently available for gene editing. These multidomain proteins can cleave DNA by recognizing a protospacer-adjacent motif (PAM) region and specifically using an RNA as a guide. In the case of the Cas12a protein, crRNA (CRISPR-RNA) is used as a guide. The RNA-DNA complementarity is essential for sequence-specific target DNA cleavage by Cas proteins. Within these proteins is a long arginine rich helix called bridge helix (BH) that is indispensable for their activity. The BH connects the nuclease (NUC) and recognition (REC) lobes. The NUC lobe is significant as it contains the domain responsible for PAM recognition and the endonuclease domain, RuvC. We recently showed that the BH region in Cas9 influences selectivity in target DNA cleavage. It is of interest to identify the role of the BH region for DNA cleavage specificity by Cas12 proteins. It is to that end that the present disclosure is directed.

BRIEF DESCRIPTION OF THE DRAWINGS

FIG. 1 shows the amino acid sequence of *Francisella tularensis* novicida strain U112 Cas12a (FnCas12a) protein (SEQ ID NO:1). The bridge helix (BH) sequence is represented in boldface.

FIG. 2 shows the amino acid sequence of Lachnospiraceae *bacterium* strain ND2006 Cas12a (LbCas12a) protein (SEQ ID NO:2). The bridge helix (BH) sequence is represented in boldface.

FIG. 3 shows the amino acid sequence of *Acidaminococcus* sp strain BV3L6 Cas12a (AsCas12a) protein (SEQ ID NO:3). The bridge helix (BH) sequence is represented in boldface.

FIG. 4 shows the amino acid sequence of *Alicyclobacillus acidoterrestris* strain 49025 Cas12b (AaCas12b) protein (SEQ ID NO:4). The bridge helix (BH) sequence is represented in boldface.

DETAILED DESCRIPTION

The present disclosure is directed to variant Cas12a and Cas 12b proteins comprising at least one amino acid substitution in the bridge helix (BH) portion of the protein, and which have improved DNA cleavage selectivity in comparison to the wild type version of the Cas12a or Cas12b protein, respectively. Certain embodiments comprise at least two amino acid substitutions in the BH portion. In particular embodiments, the at least one substitution or at least two substitutions are to proline. In certain embodiments, the present disclosure is also directed to BH variants of Cas12a from *Francisella tularensis* novicida U112, Lachnospiraceae *bacterium*, and *Acidaminococcus* sp, and of Cas12b from *Alicyclobacillus acidoterrestris*.

More particularly, certain non-limiting embodiments include, in Cas12a from *Francisella tularensis* novicida U112, substitutions in any one or more of positions 956, 957, 961, 962, 969, and 970 of the amino acid sequence SEQ ID NO: 1. The at least one amino acid substitution in the modified BH region may be selected from the group of amino acids consisting of ala, arg, asn, asp, cys, glu, gln, gly, his, ile, leu, lys, met, phe, pro, ser, thr, trp, tyr, and val. In non-limiting embodiments, the wild type amino acid may be substituted with proline, e.g., Lysine 956 and/or Leucine 957 mutated to Proline 956 and/or Proline 957, respectively; Glutamic acid 961 and/or Lysine 962 mutated to Proline 961 and/or Proline 962, respectively; and Lysine 969 and/or Aspartic acid 970 mutated to Proline 969 and/or Proline 970, respectively.

Other embodiments include, in Cas12a from Lachnospiraceae *bacterium*, substitutions in any one or more of positions 875, 876, 880, 881, 888, and 889 of the amino acid sequence SEQ ID NO:2. The at least one amino acid substitution in the modified BH region may be selected from the group of amino acids consisting of ala, arg, asn, asp, cys, glu, gln, gly, his, ile, leu, lys, met, phe, pro, ser, thr, trp, tyr, and val. In non-limiting embodiments, the wild type amino acid may be substituted with proline, e.g., Leu 875 and/or Leu 876 mutated to Proline 875 and/or Proline 876, respectively; Glu 880 and/or Lys 881 mutated to Proline 880 and/or Proline 881, respectively; and Gln 888 and/or Asn 889 mutated to Proline 888 and/or Proline 889, respectively.

Other embodiments include, in Cas12a from *Acidaminococcus* sp, substitutions in any one or more of positions 943, 944, 948, 949, 956, and 957, of the amino acid sequence SEQ ID NO:3. The at least one amino acid substitution in the modified BH region may be selected from the group of amino acids consisting of ala, arg, asn, asp, cys, glu, gln, gly, his, ile, leu, lys, met, phe, pro, ser, thr, trp, tyr, and val. In non-limiting embodiments, the wild type amino acid may be substituted with proline, e.g., Lys 943 and/or Leu 944 mutated to Proline 943 and/or Proline 944, respectively; Glu 948 and/or Lys 949 mutated to Proline 948 and/or Proline 949, respectively; and Gln 956 and/or Ala 957 mutated to Proline 956 and/or Proline 957, respectively.

Other embodiments include, in Cas12b from *Alicyclobacillus acidoterrestris*, substitutions in any one or more of positions 628-658 of the amino acid sequence SEQ ID NO:4. The at least one amino acid substitution in the modified BH region may be selected from the group of amino acids consisting of ala, arg, asn, asp, cys, glu, gln, gly, his, ile, leu, lys, met, phe, pro, ser, thr, trp, tyr, and val. In non-limiting embodiments, the wild type amino acid may be substituted with proline, e.g., Leu 63 land/or Arg 632 mutated to Pro 631 and/or Pro 632, respectively; Gln 644 and/or Leu 645 mutated to Pro 644 and/or Pro 645, respectively; Leu 654 and/or Leu 655 mutated to Pro 654 and/or Pro 655, respectively; and/or Leu 655 and/or Val 656 mutated to Pro 655 and/or Pro 656, respectively.

Before further description of various embodiments of the present disclosure in more detail by way of exemplary description, examples, and results, it is to be understood that the present disclosure is not limited in application to the details of methods, constructs, cells, and compositions as set forth in the following description. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that other embodiments of the inventive concepts may be practiced without these specific details. In other instances, features which are well known to persons of ordinary skill in the art have not been described in detail to avoid unnecessary complication of the description.

All patents, published patent applications, and non-patent publications referenced in any portion of this application, including U.S. Ser. No. 16/570,555, filed Sep. 13, 2019, and U.S. Provisional Patent Application Ser. Nos. 62/730,890, filed on Sep. 13, 2018, and 62/870,472, filed on Jul. 3, 2019, are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art.

As utilized in accordance with the methods, compounds, and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. Further, unless otherwise required by context, singular terms shall include pluralities and plural terms shall include the singular. Where used herein, the specific term "single" is limited to only "one". Use of the word "we" as a pronoun herein refers generally to laboratory personnel or other contributors who assisted in laboratory procedures and data collection and is not intended to represent an inventorship role by said laboratory personnel or other contributors in any subject matter disclosed herein.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the constructs, cells, compositions and methods used, or the variation that exists among the study objects. Further, in this detailed description and the appended claims, each numerical value (e.g., temperature or time) should be read once as modified by the term "about" (unless already expressly so modified), and then read again as not so modified unless otherwise indicated in context. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

Also, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1). Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 1-20, 10-50, 50-100, 100-1,000, 1,000-3,000, 2,000-4,000, etc.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

Protein variants disclosed herein may comprise conservative substitutions in portions of the BH region, as well as in other regions and domains of the protein. Substitutions may be selected from the natural amino acids. The natural amino acids include and may be referred to herein by the following designations: alanine: ala or A; arginine: arg or R; asparagine: asn or N; aspartic acid: asp or D; cysteine: cys or C; glutamic acid: glu or E; glutamine: gln or Q; glycine: gly or G; histidine: his or H; isoleucine: ile or I; leucine: leu or L; lysine: lys or K; methionine: met or M; phenylalanine: phe or F; proline: pro or P; serine: ser or S; threonine: thr or T; tryptophan: trp or W; tyrosine: tyr or Y; and valine: val or V. Amino acids may be D or L enantiomers.

For purposes of classifying amino acids substitutions as conservative or nonconservative, amino acids are grouped in one embodiment as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same group. Nonconservative substitutions constitute exchanging a member of one of these groups for a member of another.

Tables of exemplary conservative amino acid substitutions have been constructed and are known in the art. In certain embodiments herein which reference possible substitutions, examples of interchangeable amino acids include, but are not limited to the following: arginine and lysine; glutamate and aspartate; serine and threonine; glutamine and asparagine; and valine, leucine and isoleucine. In other embodiments, the following substitutions can be made: Ala (A) by leu, ile, or val; Arg (R) by gln, asn, or lys; Asn (N) by his, asp, lys, arg, or gln; Asp (D) by asn, or glu; Cys (C) by ala, or ser; Gln (Q) by glu, or asn; Glu (E) by gln, or asp; Gly (G) by ala; His (H) by asn, gln, lys, or arg; Ile (I) by val, met, ala, phe, or leu; Leu (L) by val, met, ala, phe, or ile; Lys (K) by gln, asn, or arg; Met (M) by phe, ile, or leu; Phe (F) by leu, val, ile, ala, or tyr; Pro (P) by ala; Ser (S) by thr; Thr (T) by ser; Trp (W) by phe, or tyr; Tyr (Y) by trp, phe, thr, or ser; and Val (V) by ile, leu, met, phe, or ala.

Other considerations for amino acid substitutions include whether or not the residue is located in the interior of a protein or is solvent- (i.e., externally) exposed. For interior residues, conservative substitutions include for example: Asp and Asn; Ser and Thr; Ser and Ala; Thr and Ala; Ala and Gly; Ile and Val; Val and Leu; Leu and Ile; Leu and Met; Phe and Tyr; and Tyr and Trp. For solvent-exposed residues, conservative substitutions include for example: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; and Phe and Tyr.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally-occurring purine or pyrimidine base found in DNA (e.g., an adenine "A," a guanine "G," a thymine "T" or a cytosine "C") or RNA (e.g., an "A," a "G," a uracil "U" or a "C"). The term nucleobase also includes non-natural bases as described below. The term "nucleic acid" encompasses the terms "oligonucleotide" and "polynucleotide," each as a subgenus of the term "nucleic acid." In certain embodiments, the present disclosure is directed to nucleic acids (DNA and RNA) which encode the variant Cas9 proteins described.

As used herein, the terms "complementary" or "complement" also refer to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In at least certain embodiments, the Cas12 variants described herein have at least 90% identity, or at least 91% identity, or at least 92% identity, or at least 93% identity, or at least 94% identity, or at least 95% identity, or at least 96% identity, or at least 97% identity, or at least 98% identity, or at least 99% identity to the corresponding wild type versions of the Cas12 proteins.

The term "homologous" or "% identity" as used herein means a nucleic acid (or fragment thereof), or a protein (or a fragment thereof) having a degree of homology to the corresponding natural reference nucleic acid, or protein, that is at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% identical thereto. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877.

Percentage sequence identities can be determined with protein sequences maximally aligned by the Kabat numbering convention. After alignment, if a particular polypeptide region is being compared with the same region of a reference polypeptide, the percentage sequence identity between the subject and reference polypeptide region is the number of positions occupied by the same amino acid in both the subject and reference polypeptide region divided by the total number of aligned positions of the two regions, with gaps not counted, multiplied by 100 to convert to percentage.

In one embodiment "% identity" represents the number of amino acids which are identical at corresponding positions in two sequences of a protein having the same or similar activity. For example, two amino acid sequences each having 100 residues will have at least 90% identity when 90 of the amino acids at corresponding positions are the same. Similarly, in one embodiment "% identity" represents the number of nucleotides which are identical at corresponding positions in two sequences of a nucleic acid encoding the same or similar polypeptides. For example, two nucleic acid sequences each having 100 nucleotides will have 90% identity when 90 of the nucleotides in homologous positions are the same.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988, 85, 2444-2448.

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

As used herein, "hybridization," "hybridizes" or "capable of hybridizing" is understood to mean the forming of a double or triple stranded molecule or a molecule with partial double or triple stranded nature. The term "anneal" as used herein is synonymous with "hybridize." The term "hybridization," "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Non-limiting applications include isolating a nucleic acid, such as a gene or a nucleic acid segment thereof, or detecting at least one specific mRNA transcript or a nucleic acid segment thereof, and the like. Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid, the length and nucleobase content of the target sequence, the charge composition of the nucleic acid, and to the presence or concentration of formamide, tetramethylammonium chloride or other solvent in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned varying conditions of hybridization to achieve varying degrees of selectivity of a nucleic acid towards a target sequence are used. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suit a particular application.

In certain embodiments herein, a "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide. As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or the like.

The term encoding" as used herein refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence" or "nucleic acid" encoding an amino acid sequence includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "bind," "binds," or "interacts with" means that one molecule recognizes and adheres to a particular second molecule in a sample or organism, but does not substantially recognize or adhere to other structurally unrelated molecules in the sample.

By the term "specifically binds," as used herein with respect to an antibody, is meant an antibody which recognizes a specific antigen, but does not substantially recognize or bind other molecules in a sample.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence of interest), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which includes an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, et al. Examples of viral vectors include, but are not limited to, adenoviral vectors, adeno-associated virus vectors, and retroviral vectors. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by attenuating the HIV virulence genes, for example, the genes env, vif, vpr, vpu, and nef are deleted making the vector biologically safe. In other embodiments of the present disclosure, a gamma retrovirus may be used as the transfecting agent.

Where used herein the term "wild-type" refers to the typical form (genotype and/or phenotype) of a bacterium, gene, nucleic acid, protein, or peptide as it occurs in nature and/or is the most common form in a natural population. In reference to a gene or nucleic acid, the term "mutation" refers to a gene or nucleic acid comprising an alteration in the wild type, such as but not limited to, a nucleotide deletion, insertion, and/or substitution. A mutation in a gene or nucleic acid generally results in either inactivation, decrease in expression or activity, increase in expression or activity, or another altered property of the gene or nucleic acid. In reference to a protein, the term "mutation" or "variant" refers to a protein comprising an alteration in the wild type, such as but not limited to, one or more amino acid deletions, insertions, and/or substitutions. A mutation in a protein may result in either inactivation, a decrease in activity or effect (e.g., binding), or an increase in activity or effect (e.g., binding or selectivity), or another altered property or effect of the protein.

In at least certain embodiments, the present disclosure is directed to a variant Cas12 protein, comprising: a nuclease (NUC) lobe, a recognition (REC) lobe, and a modified bridge helix (BH) region joining the NUC lobe and the REC lobe, the variant Cas12 protein having increased DNA cleavage selectivity relative to a corresponding wild type Cas12 protein, wherein the modified BH region increases the DNA cleavage selectivity of the variant Cas12 protein relative to the DNA cleavage selectivity of the corresponding wild type Cas12 protein, and wherein the modified BH region comprises at least one amino acid substitution relative to the corresponding wild type Cas12 protein. The at least one amino acid substitution in the modified BH region may be selected from the group consisting of ala, arg, asn, asp, cys, glu, gln, gly, his, ile, leu, lys, met, phe, pro, ser, thr, trp, tyr, and val. The at least one amino acid substitution in the modified BH region may comprise a substitution in any one or more of amino acid positions 956, 957, 961, 962, 969, and 970, wherein said amino acid positions are numbered relative to a Francisella tularensis novicida Cas12a (FnCas12a) protein set forth in of the amino acid sequence SEQ ID NO:1, and wherein the variant Cas12a protein has at least 90% identity to SEQ ID NO:1. The variant of SEQ ID NO:1 may comprise at least a pair of substitutions selected from the group consisting of (a) substitutions in amino acid positions 956 and 957, (b) substitutions in amino acid positions 961 and 962, and (c) substitutions in amino acid positions 969 and 970. The at least one amino acid substitution in the modified BH region comprises a substitution in any one or more of amino acid positions 875, 876, 880, 881, 888, and 889, wherein said amino acid positions are numbered relative to a Lachnospiraceae bacterium Cas12a (LbCas12a) protein set forth in of the amino acid sequence SEQ ID NO:2, and wherein the variant Cas12a protein has at least 90% identity to SEQ ID NO:2. The variant of SEQ ID NO:2 may comprise at least a pair of substitutions selected from the group consisting of (a) substitutions in amino acid positions 875 and 876, (b) substitutions in amino acid positions 880 and 881, and (c) substitutions in amino acid positions 888 and 889. The at least one amino acid substitution in the modified BH region comprises a substitution in any one or more of amino acid positions 943, 944, 948, 949, 956, and 957, wherein said amino acid positions are numbered relative to a Acidaminococcus sp strain BV3L6 Cas12a (AsCas12a) protein set forth in of the amino acid sequence SEQ ID NO:3, and wherein the variant Cas12a protein has at least 90% identity to SEQ ID NO:3. The variant of SEQ ID NO:3 may comprise at least a pair of substitutions selected from the group consisting of (a) substitutions in amino acid positions 943 and 944, (b) substitutions in amino acid positions 948 and 949, and (c) substitutions in amino acid positions 956 and 957. The at least one amino acid substitution in the modified BH region comprises a substitution in any one or more of amino acid positions 631, 632, 644, 645, 654, 655, and 656, wherein said amino acid positions are numbered relative to a Alicyclobacillus acidoterrestris strain ATCC 49025 Cas12b (AaCas12b) protein set forth in of the amino acid sequence SEQ ID NO:4, and wherein the variant Cas12b protein has at least 90% identity to SEQ ID NO:4. The variant of SEQ ID NO:4 may comprise at least a pair of substitutions selected from the group consisting of (a) substitutions in amino acid positions 631 and 632, (b) substitutions in amino acid positions 644 and 645, (c) substitutions in amino acid positions 654 and 655, and (d) substitutions in amino acid positions 655 and 656. In other embodiments, the present disclosure is directed to a nucleic acid which encodes any of the variants described herein. The nucleic acid may be operably linked to a transcription control sequence. The nucleic acid may be disposed in an expression vector. In other embodiments, the present disclosure is directed to a cell comprising the expression vector. The cell may further comprise a nucleic acid comprising or encoding a guide RNA that directs the variant Cas12 protein to a target genomic sequence. In other embodiments, the present disclosure is directed to system comprising the variant Cas12 protein, and a Cas12 guide RNA. In other embodiments, the present disclosure is directed to method of gene editing, comprising using a variant Cas12 protein as described elsewhere herein in a CRISPR-Cas gene-editing procedure. For example, the variant Cas12 protein may be selected from the group consisting of: (a) a variant wherein the at least one amino acid substitution in the modified BH region comprises a substitution in any one or more of amino acid positions 956, 957, 961, 962, 969, and 970, wherein said amino acid positions are numbered relative to a Francisella tularensis novicida Cas12a (FnCas12a) protein set forth in of the amino acid sequence SEQ ID NO:1, and wherein the variant Cas12a protein has at least 90% identity to SEQ ID NO:1; (b) a variant wherein the at least one amino acid substitution in the modified BH region comprises a substitution in any one or more of amino acid positions 875, 876, 880, 881, 888, and 889, wherein said amino acid positions are numbered relative to a Lachnospiraceae bacterium Cas12a (LbCas12a) protein set forth in of the amino acid sequence SEQ ID NO:2, and wherein the variant Cas12a protein has at least 90% identity to SEQ ID NO:2; (c) a variant wherein the at least one amino acid substitution in the modified BH region comprises a substitution in any one or more of amino acid positions 943, 944, 948, 949, 956, and 957, wherein said amino acid positions are numbered relative to a Acidaminococcus sp strain BV3L6 Cas12a (AsCas12a) protein set forth in of the amino acid sequence SEQ ID NO:3, and wherein the variant Cas12a protein has at least 90% identity to SEQ ID NO:3; and (d) a variant wherein the at least one amino acid substitution in the modified BH region comprises a substitution in any one or more of amino acid positions 631, 632, 644, 645, 654, 655, and 656, wherein said amino acid positions are numbered relative to a Alicyclobacillus acidoterrestris strain ATCC 49025 Cas12b (AaCas12b) protein set forth in of the amino acid sequence SEQ ID NO:4, and wherein the variant Cas12b protein has at least 90% identity to SEQ ID NO:4.

It will be understood from the foregoing description that various modifications and changes may be made in the various embodiments of the present disclosure without departing from their true spirit. The description provided herein is intended for purposes of illustration only and is not intended to be construed in a limiting sense, except where specifically indicated. Thus, while the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the formulation of the various components and compositions described herein, the methods described herein or in the steps or the sequence of steps of the methods described herein without departing from the spirit and scope of the present disclosure.

What is claimed is:

1. A variant Cas12 protein, comprising: a nuclease (NUC) lobe, a recognition (REC) lobe, and a modified bridge helix (BH) region joining the NUC lobe and the REC lobe, the variant Cas12 protein having increased DNA cleavage selectivity relative to a corresponding wild type Cas12 protein, wherein the modified BH region increases the DNA cleavage selectivity of the variant Cas12 protein relative to the DNA cleavage selectivity of the corresponding wild type Cas12 protein, and wherein the modified BH region comprises at least one amino acid substitution relative to the corresponding wild type Cas12 protein, and wherein the at least one amino acid substitution in the modified BH region comprises a substitution in any one or more of amino acid positions 956, 957, 961, 962, 969, and 970, wherein said amino acid positions are numbered relative to a *Francisella tularensis* novicida Cas12a (FnCas12a) protein set forth in of the amino acid sequence SEQ ID NO:1, and wherein the variant Cas12a protein has at least 90% identity to SEQ ID NO:1.

2. The variant Cas12 protein of claim 1, wherein the at least one amino acid substitution in the modified BH region is selected from the group consisting of ala, arg, asn, asp, cys, glu, gln, gly, his, ile, leu, lys, met, phe, pro, ser, thr, trp, tyr, and val.

3. The variant Cas12 protein of claim 1, comprising at least a pair of substitutions selected from the group consisting of (a) substitutions in amino acid positions 956 and 957, (b) substitutions in amino acid positions 961 and 962, and (c) substitutions in amino acid positions 969 and 970.

4. A variant Cas12 protein, comprising: a nuclease (NUC) lobe, a recognition (REC) lobe, and a modified bridge helix (BH) region joining the NUC lobe and the REC lobe, the variant Cas12 protein having increased DNA cleavage selectivity relative to a corresponding wild type Cas12 protein, wherein the modified BH region increases the DNA cleavage selectivity of the variant Cas12 protein relative to the DNA cleavage selectivity of the corresponding wild type Cas12 protein, and wherein the modified BH region comprises at least one amino acid substitution relative to the corresponding wild type Cas12 protein, and wherein the at least one amino acid substitution in the modified BH region comprises a substitution in any one or more of amino acid positions 943, 944, 948, 949, 956, and 957, wherein said amino acid positions are numbered relative to a *Acidaminococcus* sp strain BV3L6 Cas12a (AsCas12a) protein set forth in of the amino acid sequence SEQ ID NO:3, and wherein the variant Cas12a protein has at least 90% identity to SEQ ID NO:3.

5. The variant Cas12 protein of claim 4, comprising at least a pair of substitutions selected from the group consisting of (a) substitutions in amino acid positions 943 and 944, (b) substitutions in amino acid positions 948 and 949, and (c) substitutions in amino acid positions 956 and 957.

6. The variant Cas12 protein of claim 4, wherein the at least one amino acid substitution in the modified BH region is selected from the group consisting of ala, arg, asn, asp, cys, glu, gln, gly, his, ile, leu, lys, met, phe, pro, ser, thr, trp, tyr, and val.

7. A method of gene editing, comprising using a variant Cas12 protein in a CRISPR-Cas gene-editing procedure, wherein the variant Cas12 protein comprises a nuclease (NUC) lobe, a recognition (REC) lobe, and a modified bridge helix (BH) region joining the NUC lobe and the REC lobe, the variant Cas12 protein having increased DNA cleavage selectivity relative to a corresponding wild type Cas12 protein, wherein the modified BH region increases the DNA cleavage selectivity of the variant Cas12 protein relative to the DNA cleavage selectivity of the corresponding wild type Cas12 protein, and wherein the modified BH region comprises at least one amino acid substitution relative to the corresponding wild type Cas12 protein, and wherein the variant Cas12 protein is a variant Cas12a protein wherein the at least one amino acid substitution in the modified BH region comprises a substitution in any one or more of amino acid positions 956, 957, 961, 962, 969, and 970, wherein said amino acid positions are numbered relative to a *Francisella tularensis* novicida Cas12a (FnCas12a) protein set forth in of the amino acid sequence SEQ ID NO:1, and wherein the variant Cas12a protein has at least 90% identity to SEQ ID NO:1.

8. The method of claim 7, wherein the variant Cas12a comprises at least a pair of substitutions selected from the group consisting of (a) substitutions in amino acid positions 956 and 957, (b) substitutions in amino acid positions 961 and 962, and (c) substitutions in amino acid positions 969 and 970.

9. A method of gene editing, comprising using a variant Cas12 protein in a CRISPR-Cas gene-editing procedure, wherein the variant Cas12 protein comprises a nuclease (NUC) lobe, a recognition (REC) lobe, and a modified bridge helix (BH) region joining the NUC lobe and the REC lobe, the variant Cas12 protein having increased DNA cleavage selectivity relative to a corresponding wild type Cas12 protein, wherein the modified BH region increases the DNA cleavage selectivity of the variant Cas12 protein relative to the DNA cleavage selectivity of the corresponding wild type Cas12 protein, and wherein the modified BH region comprises at least one amino acid substitution relative to the corresponding wild type Cas12 protein, and wherein the variant Cas12 protein is a variant Cas12a protein wherein the at least one amino acid substitution in the modified BH region comprises a substitution in any one or more of amino acid positions 943, 944, 948, 949, 956, and 957, wherein said amino acid positions are numbered relative to a *Acidaminococcus* sp strain BV3L6 Cas12a (AsCas12a) protein set forth in of the amino acid sequence SEQ ID NO:3, and wherein the variant Cas12a protein has at least 90% identity to SEQ ID NO:3.

10. The method of claim 9, wherein the variant Cas12a protein comprises at least a pair of substitutions selected from the group consisting of (a) substitutions in amino acid positions 943 and 944, (b) substitutions in amino acid positions 948 and 949, and (c) substitutions in amino acid positions 956 and 957.

* * * * *